United States Patent [19]

Warner

[11] 4,092,635
[45] May 30, 1978

[54] HUMIDITY SENSOR ALARM UNIT

[75] Inventor: Roger M. Warner, Bethesda, Md.

[73] Assignee: Baxter Travenol Laboratories, Inc., Deerfield, Ill.

[21] Appl. No.: 724,811

[22] Filed: Sep. 20, 1976

[51] Int. Cl.² .............................................. G08B 21/00
[52] U.S. Cl. ...................................... 340/235; 340/409
[58] Field of Search ................................ 340/235, 409

[56] References Cited

U.S. PATENT DOCUMENTS

| 2,752,586 | 6/1956 | Jordan | 340/235 |
| 2,832,947 | 4/1958 | Patchell | 340/409 |
| 3,197,699 | 7/1965 | Johansen | 340/235 |
| 3,588,891 | 6/1971 | Porter | 340/409 |
| 3,599,862 | 8/1971 | Hogan | 340/235 |
| 3,771,548 | 11/1973 | Rauchwerger | 340/235 |
| 3,898,423 | 8/1975 | Taylor | 340/235 |
| 3,902,040 | 8/1975 | Ikeda | 340/235 |
| 3,950,740 | 4/1976 | Greene | 340/235 |
| 4,035,787 | 7/1977 | Hornung | 340/409 |

Primary Examiner—Thomas B. Habecker
Attorney, Agent, or Firm—H. W. Collins; Richard G. Kinney; Eugene M. Cummings

[57] ABSTRACT

An alarm unit for a humidity sensor activates an alarm circuit when the relative humidity rises above a certain value or under certain malfunction conditions such as a missing sensor or a cut cable, includes a first circuit for establishing a reference signal, and a second circuit adapted to be connected to a humidity sensor for responding thereto and for generating a humidity out-of-limits signal. A third circuit responds to the reference signal and to the humidity out-of-limits signal to generate an alarm signal. The third circuit includes a level detector, and the first circuit comprises an impedance device which cooperates with the second circuit which in turn connects the sensor to the input of the level detector, the sensor being a variable impedance device.

4 Claims, 1 Drawing Figure

U. S. Patent        May 30, 1978        4,092,635
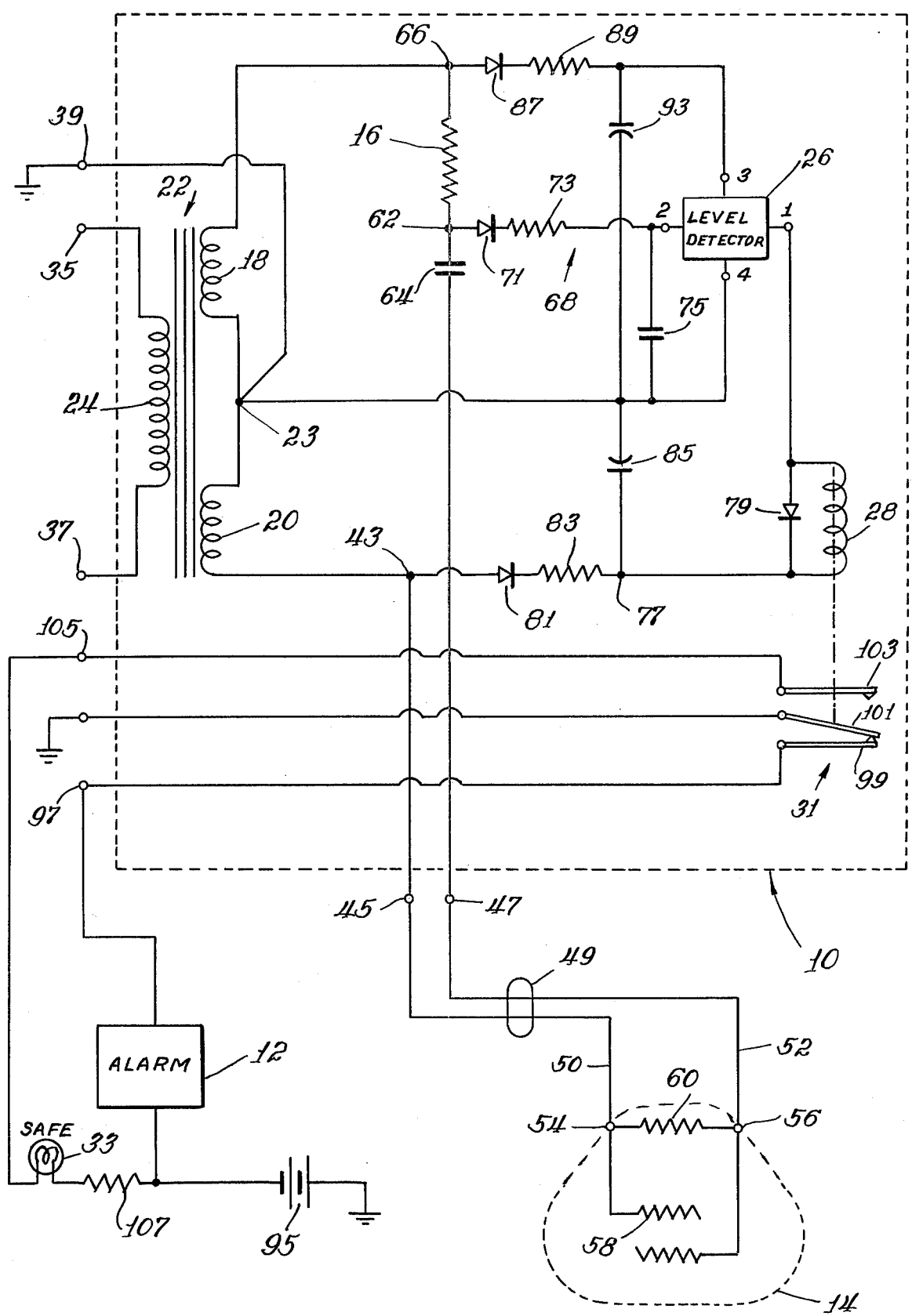

HUMIDITY SENSOR ALARM UNIT

BACKGROUND OF THE INVENTION

The present invention relates in general to a humidity sensor alarm unit, and it more particularly relates to a fail-safe alarm unit which activates an alarm circuit when the relative humidity changes to an out-of-limit condition or when a malfunction such as a power failure or cut cable occurs.

Electrical humidity sensors have been employed for detecting relative humidity. Such sensors employ hygroscopic film which changes its electrical resistance rapidly with minute changes in moisture conditions. While such humidity sensors have been employed successfully for many different applications, it would be highly desirable to have a humidity sensor detecting an out-of-limit humidity condition or when certain malfunction conditions occur, such conditions including the humidity sensor circuit being shorted or opened. In this regard, the alarm signal should be generated when a cable is cut or the humidity sensor is missing. Also, the alarm signal should be generated when a power failure occurs, or when any circuit component of the alarm unit should fail.

SUMMARY OF THE INVENTION

Therefore, it is an object of the present invention to provide a new and improved humidity sensor alarm circuit, which generates an alarm signal when the relative humidity changes to an out-of-limits condition or when certain malfunctions occur.

This and further objects of the present invention are attained by providing an alarm unit for a humidity sensor, which unit includes a first circuit for establishing a reference signal, and a second circuit adapted to be connected to the sensor for responding thereto to generate a humidity out-of-limits signal. A third circuit responds to the reference signal and to the humidity out-of-limits signal to generate an alarm signal. The third circuit includes a level detector, and the first circuit comprises an impedance device which cooperates with the second circuit which in turn connects the sensor to the input of the level detector, the sensor being a variable impedance device.

In one embodiment of the present invention, the first circuit and the second circuit are connected and arranged to form a bridge circuit, and the level detector is connected in the bridge circuit as a null voltage detector. A separate relay circuit is normally energized during the safe condition by the level detector until the humidity sensor changes its impedance to cause the relay circuit via the level detector to become de-energized, thereby generating the alarm signal. The alarm contacts of the relay are included in a separate battery supply circuit.

DESCRIPTION OF THE DRAWING

The above, and still further highly important objects and advantages of the invention will become apparent from the following detailed specification, appended claims, and attached drawing, which is a schematic circuit diagram of the humidity sensor alarm unit constructed in accordance with the present invention.

DESCRIPTION OF A PREFERRED EMBODIMENT

Referring now to the drawing, there is shown a humidity sensor alarm unit 10, which is constructed in accordance with the present invention and which is adapted to energize an attention attracting alarm device 12 when an electrical variable-resistance humidity sensor 14 detects that the ambient humidity exceeds a certain predetermined value, or when a malfunction occurs. The humidity sensor alarm unit 10 generally comprises a bridge circuit which has four elements and which is balanced to provide a null indication. The four elements generally comprise the sensor 14, a resistor 16, and the two output windings 18 and 20 of a transformer 22, which has a grounded center tap 23 and an input winding 24. In order to detect a null condition of the bridge arrangement, the input circuit across terminals 2 and 4 of an integrated circuit level detector 26 senses voltage levels between the center tap 23 and the resistory 16. A relay coil 28 is connected to the output terminal 1 of the level detector 26, which is energized during a normal safe condition which is de-energized when an alarm condition occurs as hereinafter described in greater detail. A set of transfer contacts 31 of the relay 28 energizes an indicator lamp 33 to designate a "SAFE" condition during normal operation and to activate the alarm device 12 during an alarm condition when the relay 28 is de-energized.

In oepration, the component values of the alarm unit 10 are chosen so that during a normal safe operation the input circuit across teminals 2 and 4 of the level detector 26 is at a low voltage or null condition. The voltage level at the output terminal 1 of the level detector 26 is controlled by the voltage level at the input terminals 2 and 4 of the level detector 26. In this regard, decreasing the voltage level across the input terminals 2 and 4 of the level detector 26 causes the output terminal 1 relative to the terminal 4 of the level detector 26 to be switched to an ON state, and increasing the input voltage level across the terminals 2 and 4 causes the output terminal 1 relative to the terminal 4 to switch to its OFF state. Thus, with the bridge circuit arrangement, the voltage level across the input terminals 2 and 4 increases with both decreasing and increasing resistance of the sensor 14. The output terminal 1 is switched to its OFF condition at both high and low sensor resistance conditions. Thus, the relay 28 is normally energized during the safe operation of the unit, and the relay 28 is de-energized in the OFF state of the level detector 26 to enable the alarm device 12 to be activated.

Considering now the alarm unit 10 in greater detail, a pair of input terminals 35 and 37 are adapted to be connected to a 60 cycles per second 110 volts AC line potential and is connected across the input winding 24 of the transformer 22. A grounded terminal 39 is connected to the center tap 23 of the output windings of the transformer 22.

A point 43 has connected thereto one end of the output winding 20 of the transformer 22 and a terminal 45 of a pair of terminals 45 and 47 which have a cable 49 comprising leads 50 and 52 connected thereto. A pair of terminals 54 and 56 of the sensor 14 are connnected respectively to the other ends of the leads 50 and 52 of the cable 49, whereby the sensor 14 may be disposed remotely of the alarm unit 10. The terminals 54 and 56 represent sockets of the humidity sensor 14, which is mounted in an aluminum protective jacket (not shown).

An internal variable resistance 58 of the humidity sensor 14 changes electrical resistance with changes in relative humidity. Increasing humidity decreases the sensor internal resistance 58 and decreasing humidity increases the resistance 58. A shunting resistance 60 is connected across the resistance 58, within the jacket, so that the shunting resistance 60 becomes an integral part of the sensor 14. The value of the shunting resistance is selected so that as the relative humidity decreases, the combined circuit resistance of the internal variable resistance 58 and the shunting resistance 60 causes a low or null voltage to be established across the input terminals 2 and 4 of the level detector 26. As a result, the level detector 26 is normally in its ON state to cause the relay 28 to be activated for causing the lamp 33 to be illuminated, thereby indicating a SAFE condition.

The humidity sensor 14 may be a humidity sensor known under the trade name "HYGROSENSOR", which may be purchased from American Instrument Company (Hygrodynamics Division) of Silver Spring, Maryland. The American Instrument Company is a division of Travenol Laboratories, Inc., which is a wholly owned subsidiary of the present assignee, Baxter Travenol Laboratories, Inc.. A point 62 connected to one end of the resistor 16 is connected through a capacitor 64 to the other terminal 47. A null circuit generally indicated at 68 includes a current rectifying diode 71 which is connected between the point 62 and a current limiting resistor 73, which in turn is connected to the terminal 2 of the level detector 26. A capacitor 75 is connected across the input terminals 2 and 4 of the level detector 26, the terminal 4 being connected to the grounded center tap 23 to complete the null circuit 68.

Considering now the relay 28, the relay 28 has its coil connected between the output terminal 1 of the level detector 26 and a point 77, a diode 79 being connected across the relay coil. A current rectifying diode 81 is connected between the point 43 and a resistory 83 which in turn is connected to the point 77, a capacitor 85 connecting the point 77 to the grounded center tap 23. Thus, when the level detector 26 is in its ON state, the output terminals 1 and 4 are effectively shorted together to complete a circuit path including the grounded center tap 23, the output terminals 1 and 4 of the level detector 26, the relay coil 28, the resistor 83, the diode 81 and the output winding 20 of the transformer 22. As a result, the relay 28 becomes energized when the level detector 26 is in its ON state. The diode 79 is so polarized to facilitate the fast release of the relay 28 to cause the alarm device 12 to be activated in a rapid manner.

In order to bias the level detector 26, a current rectifying diode 87 is connected between the point 66 and a current limiting resistor 87, which in turn is connected to a supply voltage terminal 3 of the level detector 26, a capacitor 93 being connected between the terminal 3 and the grounded center tap 23. Thus, voltage is supplied to the level detector 26 by a circuit which includes the grounded center tap 23, the output winding 18 of the transformer 22, the diode 87, the resistor 89 and the voltage supply terminal 3 of the level detector 26.

The level detector 26 may be any suitable level detector, such as the Amperex TAA560 which is a silicon monolithic integrated level detector sold by Amperex Electronic Corporation of Slatersville, Rhode Island. The Amperex TAA 560 includes a Darlington input circuit that serves as a Schmitt trigger circuit followed by three amplifier stages.

Considering now the manner in which the alarm signal is generated, a grounded battery 95 is connected to the alarm device 12, which in turn is connected to a terminal 97 of the unit 10. A fixed contact 99 of the transfer contacts 31 is connected to the terminal 97 and engages a movable grounded contact 101 when the relay 28 is de-energized as shown in the drawing. A fixed contact 103 is adapted to engage the movable grounded contact 101 when the relay 28 is energized and is connected to a terminal 105, which in turn is connected to the lamp 33. A current limiting resistor 106 connects the lamp 33 to the battery 95. Thus, when the relay 28 is de-energized as shown in the drawing the movable contact 101 engages the fixed contact 99 to complete a circuit which includes the battery 95, the alarm device 12, the fixed contact 99 and the grounded movable contact 101 to energize the alarm device 12. When the relay 28 is energized, a circuit is completed to illuminate the lamp 33 without energizing the alarm device 12 by means of a circuit which includes the grounded movable contact 101, the fixed contact 103, the lamp 33 and the resistor 107 to the grounded battery 95 to illuminate the lamp 33.

It should be noted that a separate battery 95 is employed to activate the alarm device 12 so that in the event of a power failure, the relay 28 would restore, and the battery 95 would then activate the alarm device 12. The lamp 33 is constantly illuminated to indicate the condition of the battery 95.

In view of the foregoing description, it should now be apparent that the alarm device 12 is energized when the relative humidity rises above a certain value, and when certain malfunctions occur. The malfunctions include a power failure, the humidity sensor 14 being accidentally short-circuited, the humidity sensor 14 being accidentally opened or removed from the circuit or any circuit component of the unit 10 failing to function properly, causing the relay 28 to become de-energized. Thus, the alarm device 12 is energized when the humidity sensor 14 is opened or removed, as well as for a low resistance or short circuit condition of the humidity sensor 14. As a result, the alarm device 12 is energized should the cable 49 be cut, or the humidity sensor 14 be removed from the circuit.

The alarm conditions are adjustable by selection of the range of humidity sensor 14 and by the selection of values of the circuit components within the range of a specific sensor. A particular humidity sensor which may be used is a Hygrodynamics humidity sensor 15-1209F.

It will also become apparent to those skilled in the art that the unit 10 could be adjusted to generate an alarm signal for low humidity conditions, or when the humidity was either low or higher than a desired value.

| Element | Component | Value |
| --- | --- | --- |
| 16 | Resistor | 910K |
| 60 | Resistor | 2–5 Meg |
| 64 | Capacitor | 0.22 mf |
| 73 | Resistor | 100 K |
| 75 | Capacitor | 0.1 mf |
| 83 | Resistor | 56 |
| 85 | Capacitor | 100 mf |
| 89 | Resistor | 180 |
| 93 | Capacitor | 100 mf |

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A fail-safe humidity sensing alarm apparatus, which comprises:
   an electric humidity sensor for detecting changes in humidity and having a resistance which varies in response to humidity variations;
   a level detector for detecting a substantially null condition and for providing a first signal when said substantially null condition is detected and a second signal when other than a substantially null condition is detected;
   a bi-stable device having a first state in response to said first signal and a second state in response to said second signal;
   alarm means for providing an alarm when said bi-stable device is in said second state; and
   circuit means for providing to said level detector (a) a substantially null condition when said humidity sensor detects a relative humidity which is below a predetermined threshold, (b) other than a substantially null condition when said humidity sensor detects a relative humidity which exceeds the predetermined threshold, (c) other than a substantially null condition when said humidity sensor is short-circuited, and (d) other than a substantially null condition when said humidity sensor is open-circuited.

2. A humidity sensing alarm apparatus as described in claim 1, said circuit means including first and second secondary windings of a transformer connected with the humidity sensor and an impedance device to form a bridge circuit with the level detector.

3. A humidity sensing alarm apparatus as described in claim 2, said circuit means further including a shunting resistance connected across said humidity sensor.

4. A humidity sensing alarm apparatus as described in claim 1, said bi-stable device comprising an electromagnetic relay having a plurality of relay contacts, said relay contacts being operative to close an alarm circuit when said relay is in said second state and to open said alarm circuit when said relay is in said first state.

* * * * *